United States Patent
Arramon et al.

(10) Patent No.: US 11,819,424 B2
(45) Date of Patent: Nov. 21, 2023

(54) ROBOT ASSISTED INTERVERTEBRAL DISC PROSTHESIS SELECTION AND IMPLANTATION SYSTEM

(71) Applicant: Simplify Medical Pty Ltd, Paddington (AU)

(72) Inventors: Yves Arramon, Sunnyvale, CA (US); David Hovda, Mountain View, CA (US); Michael Sherman, Memphis, TN (US)

(73) Assignee: Simplify Medical Pty Ltd, Sunnyvale, CA (US)

( * ) Notice: Subject to any disclaimer, the term of this patent is extended or adjusted under 35 U.S.C. 154(b) by 566 days.

(21) Appl. No.: 16/578,949

(22) Filed: Sep. 23, 2019

(65) Prior Publication Data

US 2020/0093613 A1 Mar. 26, 2020

Related U.S. Application Data

(60) Provisional application No. 62/735,701, filed on Sep. 24, 2018.

(51) Int. Cl.
*A61F 2/46* (2006.01)
*A61F 2/30* (2006.01)
(Continued)

(52) U.S. Cl.
CPC ........ *A61F 2/4611* (2013.01); *A61B 17/1703* (2013.01); *A61B 17/1757* (2013.01);
(Continued)

(58) Field of Classification Search
CPC ........ A61F 2/46; A61F 2/4611; A61F 2/4657; A61F 2/4684; A61F 2/44; A61F 2/30;
(Continued)

(56) References Cited

U.S. PATENT DOCUMENTS 6,226,548 B1 5/2001 Foley et al.
6,340,363 B1 1/2002 Bolger et al.
(Continued)

FOREIGN PATENT DOCUMENTS

EP 2381858 B1 11/2018
JP 2017536909 A 12/2017
(Continued)

OTHER PUBLICATIONS

International Search Report and Written Opinion for PCT/AU2019/000115 dated Jan. 10, 2020.

*Primary Examiner* — Christopher J Beccia

(57) ABSTRACT

Systems and methods are provided for robotically assisted disc prosthesis selection and implantation. The system includes a 3D modeling system for creating a 3D model of first and second vertebra adjacent the intended surgical site and identifying and storing data for the positions of the first and second vertebrae. A computing system for stores and processes the 3D model and the position data. A robot connected to the computing system attaches to a plurality of instruments including sizing templates, trials, cutters or placement instruments for intervertebral disc prostheses. An interface on the computing system allows the surgeon to sequentially deliver the plurality of instruments with the robot to a registration position to improve the speed and accuracy of the surgical procedure.

12 Claims, 5 Drawing Sheets

(51) Int. Cl.
*A61B 90/00* (2016.01)
*A61B 34/10* (2016.01)
*A61B 17/17* (2006.01)
*A61B 34/30* (2016.01)
*A61F 2/44* (2006.01)

(52) U.S. Cl.
CPC .............. *A61B 34/10* (2016.02); *A61B 34/30* (2016.02); *A61B 90/03* (2016.02); *A61F 2/30771* (2013.01); *A61F 2/442* (2013.01); *A61F 2/4657* (2013.01); *A61F 2/4684* (2013.01); *A61B 2034/105* (2016.02); *A61B 2034/108* (2016.02); *A61B 2090/034* (2016.02); *A61F 2002/30273* (2013.01); *A61F 2002/30904* (2013.01); *A61F 2002/4633* (2013.01); *A61F 2002/4658* (2013.01); *A61F 2002/4666* (2013.01); *A61F 2002/4681* (2013.01); *A61F 2002/4687* (2013.01)

(58) Field of Classification Search
CPC ...... A61F 2/30771; A61B 90/00; A61B 90/03; A61B 34/30
See application file for complete search history.

(56) References Cited

U.S. PATENT DOCUMENTS

| | | | |
|---|---|---|---|
| 7,442,211 B2 | 10/2008 | de Villiers et al. | |
| 7,531,001 B2 | 5/2009 | De Villiers et al. | |
| 7,542,791 B2 | 6/2009 | Mire et al. | |
| 7,567,834 B2 | 7/2009 | Clayton et al. | |
| 7,575,599 B2 | 8/2009 | Villiers et al. | |
| 7,585,326 B2 | 9/2009 | De Villiers et al. | |
| 7,637,913 B2 | 12/2009 | De Villiers et al. | |
| 7,753,956 B2 | 7/2010 | De Villiers et al. | |
| 8,043,295 B2 | 10/2011 | Reed et al. | |
| 8,100,979 B2 | 1/2012 | Felt et al. | |
| 8,206,449 B2 | 6/2012 | Jansen et al. | |
| 8,337,508 B2 | 12/2012 | Lavallee et al. | |
| 8,394,144 B2 | 3/2013 | Zehavi et al. | |
| 8,685,035 B2 | 4/2014 | De Villiers et al. | |
| 8,764,833 B2 | 7/2014 | De Villiers et al. | |
| 8,840,629 B2 | 9/2014 | Bonutti | |
| 8,897,514 B2 | 11/2014 | Feikas et al. | |
| 8,992,580 B2 | 3/2015 | Bar et al. | |
| 9,011,544 B2 | 4/2015 | Arramon et al. | |
| 9,125,680 B2 | 9/2015 | Kostrzewski et al. | |
| 9,351,846 B2 | 5/2016 | De Villiers et al. | |
| 9,545,233 B2 | 1/2017 | Sirpad et al. | |
| 9,782,229 B2 | 10/2017 | Crawford et al. | |
| 10,034,711 B2 | 7/2018 | Greenwald et al. | |
| 2005/0154296 A1* | 7/2005 | Lechner | A61B 17/00234 600/429 |
| 2006/0084986 A1 | 4/2006 | Grinberg et al. | |
| 2007/0198022 A1 | 8/2007 | Lang et al. | |
| 2008/0195081 A1 | 8/2008 | Moll | |
| 2009/0234217 A1 | 9/2009 | Mire et al. | |
| 2009/0299477 A1 | 12/2009 | Clayton et al. | |
| 2011/0306873 A1* | 12/2011 | Shenai | A61B 8/0841 600/424 |
| 2014/0378999 A1* | 12/2014 | Crawford | A61B 5/066 606/130 |
| 2015/0032164 A1 | 1/2015 | Crawford et al. | |
| 2015/0366624 A1* | 12/2015 | Kostrzewski | A61B 34/76 606/130 |
| 2017/0265774 A1* | 9/2017 | Johnson | A61B 5/064 |
| 2018/0110573 A1 | 4/2018 | Kostrzewski | |
| 2018/0125598 A1 | 5/2018 | McAfee | |
| 2018/0199951 A1 | 7/2018 | Chappuis et al. | |
| 2018/0221008 A1 | 8/2018 | Todorov et al. | |
| 2019/0103190 A1* | 4/2019 | Schmidt | A61B 34/10 |

FOREIGN PATENT DOCUMENTS

| | | |
|---|---|---|
| WO | WO-2010064234 A2 | 6/2010 |
| WO | WO-2016131903 A1 | 8/2016 |
| WO | WO-2016154356 A1 | 9/2016 |
| WO | WO-2018167246 A1 | 9/2018 |
| WO | WO-2020061610 A1 | 4/2020 |

* cited by examiner

ROBOT ASSISTED INTERVERTEBRAL DISC PROSTHESIS SELECTION AND IMPLANTATION SYSTEM

CROSS-REFERENCE TO RELATED APPLICATIONS

This application claims the benefit of U.S. Provisional No. 62/735,701, filed Sep. 24, 2018, the entire content of which is incorporated herein by reference.

BACKGROUND OF THE INVENTION

1. Field of the Invention

The present invention relates to medical devices and methods. More specifically, the invention relates to intervertebral prosthetic discs and systems and methods for robotically preparing for and performing implantation of an intervertebral prosthetic disc.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

Common causes of back pain are injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs. With age, intervertebral disks begin to shrink. In some cases, they may collapse completely and cause the bones to rub against one another. This is also referred to as osteoarthritis.

When a damaged intervertebral disc causes a patient pain and discomfort, surgery is often required. Typically, surgical procedures for treating damaged intervertebral discs involve discectomy (partial or total removal of a disc), often followed by interbody fusion of the superior and inferior vertebrae adjacent to the disc or implantation of an intervertebral prosthetic disc. Fusion is most commonly achieved by implantation of a cage or spacer together with bone graft material to promote bone growth to fuse the adjacent vertebrae together. Oftentimes, pins, rods, screws, cages and/or the like are placed between the vertebrae to act as support structures to hold the vertebrae and bone graft material in place while the bones permanently fuse together. Spinal fusion eliminates motion between the vertebrae. Fusion is an option when motion is the source of pain.

An alternative to spinal fusion which doesn't limit patient mobility is intervertebral disc replacement (TDR), also called total disc arthroplasty. The TDR procedure involves removing the natural disk from between the vertebrae and replacing it with and artificial disc prosthesis. Several types of intervertebral disc prosthesis are currently available. For example, one type of intervertebral disc prosthesis includes upper and lower prosthesis plates which locate against and engage the adjacent vertebral bodies and a mobile core positioned between the plates. The core has upper and lower convexly curved surfaces and the plates have corresponding, concavely curved recesses which cooperate with the curved surfaces of the core. This allows the plates to slide over the core to allow spinal movement to take place.

In one alternative arrangement, the core is eliminated and the upper and lower prosthesis plates of the intervertebral disc prosthesis articulate about one another in a ball and socket articulation arrangement. Typical drawbacks of the known intervertebral disc prosthesis include insufficient resistance to wear and tear, restricted range of motion, undesirable contact between plates causing potential wear, excessive disc height not appropriately matched to patient anatomy and/or insufficient ability of the prosthesis to adhere to vertebral bone. These drawbacks have been acknowledged and new intervertebral disc prosthesis are being developed which have improved properties. However, positioning the intervertebral disc prosthesis accurately for optimal performance continues to be problematic.

Therefore, a need exists for improved intervertebral disc prosthesis implantation techniques. Ideally, such improved techniques would improve speed and precision for intervertebral disc prosthesis implantation surgery and reduce associated surgical blood loss and radiation exposure to patients. At least some of these objectives will be met by the inventions described herein.

2. Description of the Background Art

A variety of intervertebral disc prosthesis designs and methods of implanting are described in described in U.S. Pat. Nos. 7,442,211; 7,531,001; 7,575,599; 7,585,326; 7,637,913; 7,753,956; 8,206,449; 8,685,035; 8,764,833; 9,011,544 and 9,351,846, each of which is incorporated herein by reference in its entirety.

BRIEF SUMMARY OF THE INVENTION

According to one aspect of the invention, a surgical method for robot assisted intervertebral disc prosthesis selection comprises identifying positions of first and second vertebrae and generating and storing position data for the positions of the first and second vertebrae in a computing system; inserting a first disc sizer between the first and second vertebrae; adjusting the first disc sizer to a desired location for the selected intervertebral disc prosthesis with respect to the positions of the first and second vertebrae and registering position data for the intervertebral disc prosthesis location as a registered location; removing the first disc sizer; robotically inserting a second disc sizer and subsequent disc sizers to the registered location and removing the sizer until a desired size for the intervertebral disc prosthesis is determined; robotically inserting a cutter to the registered location to cut one or more channels in at least one of the first and second vertebrae; robotically removing the cutter; robotically inserting an intervertebral disc prosthesis corresponding in size to the desired size for the intervertebral disc prosthesis to the to the registered location with an inserter instrument; and robotically removing the inserter instrument.

According to a further aspect of the invention, a surgical method for robot assisted intervertebral disc prosthesis placement comprises identifying positions of first and second vertebrae and generating and storing position data for the positions of the first and second vertebrae in a 3D model in a computing system; inserting a first trial instrument between the first and second vertebrae to get an initial registration position with respect to the first and second bones and storing position data, wherein the initial registration position is a desired location for the selected intervertebral disc prosthesis with respect to the positions of the first and second vertebrae; sequentially delivering a plurality of instruments including sizing templates, trials, cutters or placement instruments with a robot to the initial registration position.

According to another aspect of the invention, a system for robot assisted intervertebral disc prosthesis placement comprises a 3D modeling system for creating a 3D model of first and second vertebra adjacent the disc space and identifying positions of the first and second vertebrae and generating and storing position data for the positions of the first and second vertebrae; a computing system for storing and processing the 3D model and the position data; a robot; a plurality of instruments including sizing templates, trials, cutters or placement instruments; and an interface on the computing system configured to allow the surgeon to sequentially deliver the plurality of instruments with the robot to a registration position.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
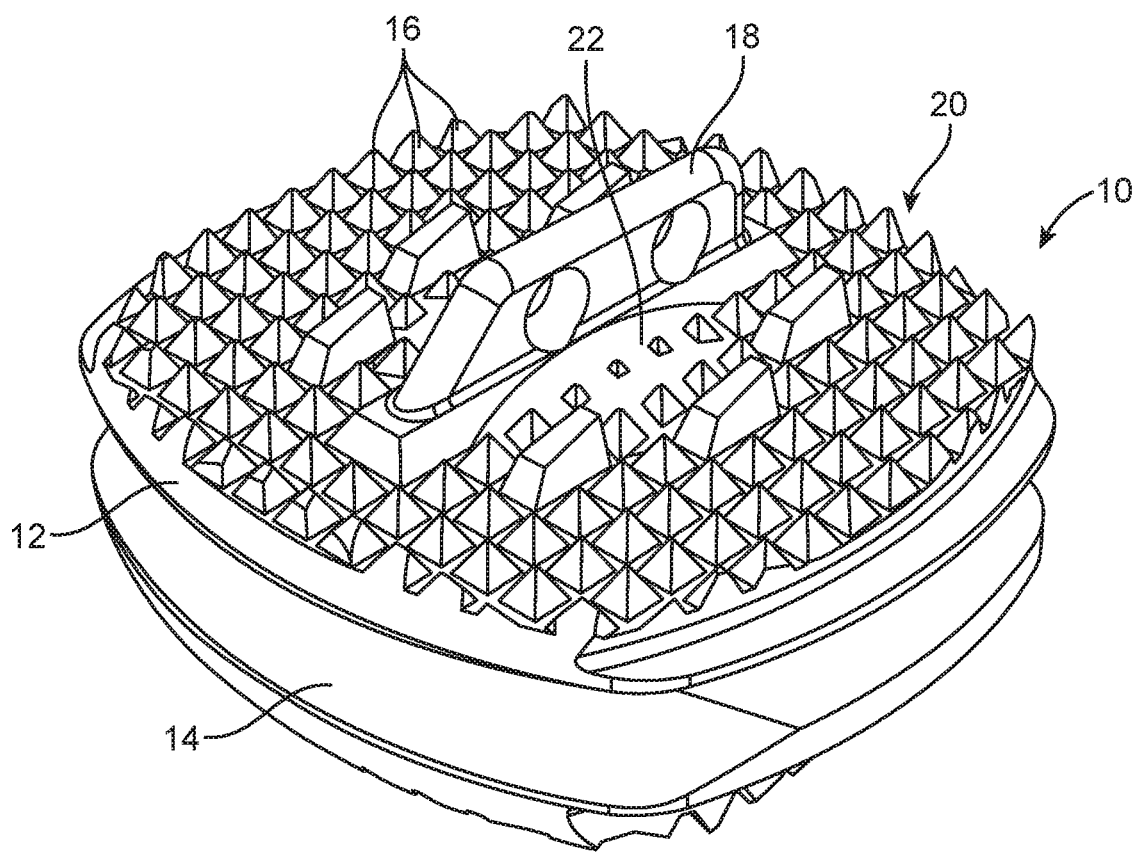
FIG. 1 is a perspective view of an intervertebral disc prosthesis with a central fin.

Positioning of an intervertebral disc prosthesis properly in the spine is an important part of a successfully total disc replacement (TDR) procedure. The position of the implant in the intervertebral space can influence the range of motion, implant behavior and clinical result. Potential improper positions include discs not placed on the midline of the adjacent vertebrae, discs not placed in the proper position in the anterior posterior direction, discs rotated within the disc space and discs in which the upper and lower disc components are not aligned with one another. Surgeon experience, surgeon training, use of imaging modalities and patient anatomy are all factors which can influence accuracy of disc placement.

The selection of a disc prosthesis appropriate for the size and anatomy of a particular patient and implantation of the selected disc prosthesis when performed in the traditional manner involves inserting multiple instruments to the same location in the spine throughout the surgery. This procedure can be time consuming and involve significant radiation exposure due to the time and verification required to locate the correct position at each instrument insertion. Further, each pass of an instrument into and out of the body has an associated risk of injury to the surrounding anatomic structures and X-ray exposure. Minimizing and/or simplifying these passes reduces the overall risk of the procedure.

In one example of a traditional procedure, first a disc prosthesis size is determined by inserting one and generally multiple trial discs in a sequential manner starting with a smallest size trial and switching to sequentially larger size trials. The surgeon views each of the trials both visually and via X-ray until an appropriate fit is confirmed. The goal of the disc prosthesis sizing process is to find the best possible anatomical fit with a largest footprint size and a smallest height needed to restore natural spine position and motion. This can be a prolonged process involving significant X-ray exposure to the patient that could be reduced if the surgeon was provided with a robot which can return multiple instruments to the same location with respect to the adjacent vertebrae. The full implantation procedure of this type may require the surgeon to place multiple sizers or trials, followed by a cutter and then finally the selected disc prosthesis with the goal of always returning with each instrument to the same desired position between the vertebrae. Each time the surgeon returns to the surgical site with an instrument the surgeon determines the instrument location by X-ray, adjusts the position as needed and confirms the adjusted position by X-ray. This leads to repeated radiation exposure and an extended surgery time that could be avoided if the surgeon had a way to robotically return to the same position with respect to the adjacent vertebrae.

The robotic assisted disc selection process uses a robotic arm to save time and improve precision in inserting multiple trial discs of different sizes (height, footprint and/or lordosis) to the same location between the vertebrae and adjusting the size and fit until an optimal fit is achieved. This robotic assisted disc selection process can be used alone or combined with robotic insertion of one or more cutters and finally robotic insertion of the intervertebral disc prosthesis with the robot always returning each instrument to the same position with respect to the two adjacent bones.

Referring to FIG. 1, one example of an intervertebral disc prosthesis 10 for insertion between adjacent vertebrae includes an upper plate 12, a lower plate 14 and a core (not shown) between the upper and lower plates. The core is retained between the upper and lower plates by a retention feature and is designed to allow the plates to slide over the upper and lower surfaces of the core in the anterior/posterior direction and in the lateral direction and to allow the plates to articulate and rotate with respect to each other and the core.

The upper plate 12 includes an outer surface 20 having a plurality of serrations 16 pyramid shapes or truncated pyramid shapes. A fin 18 extends from a center of the outer surface 20 in an anterior/posterior direction. The outer surface 20 also includes a domed shaped central portion 22 to accommodate the natural anatomical concavity in the lower surfaces of the vertebrae. The core cannot be seen between the plates, however further details of the core can be found in U.S. Pat. No. 8,764,833 which is incorporated herein by reference in its entirety.

The lower plate 14 has an outer surface which may have the same shape as the outer surface of the upper plate with a fin, dome and serrations. However, in other embodiments the upper and lower plates can have different configurations to more closely match the anatomy of the patient. For example, the upper or superior plate 12 may have a somewhat domed shaped central portion 22 to accommodate the natural anatomical concavity in the lower surfaces of the vertebra above the disc while the lower plate 14 may have a smaller dome or no dome to more closely match the anatomy of the upper surfaces of the vertebra below the disc. The upper and lower plates can both have one central fin 18 or more than one fin. In one example, the upper plate 12 has a single central fin 18 designed to be placed on the midline of the vertebrae while the lower plate 14 has two fins symmetrically place fins designed to be placed symmetrically about the midline. In addition, one or both of the upper and lower plates can be provided with non-parallel upper and lower surfaces to accommodate spinal lordosis. To accommodate different patient anatomy, the disc prosthesis 10 is preferably provided in multiple sizes including different footprint sizes (sizes having different width and depth) and different heights (distance between the outer surfaces of the two plates 12, 14) and lordosis angles (angle between the outer surfaces of the two plates 12, 14).

The robotic systems for disc prosthesis selection and implantation described below can be used to both select the appropriate size disc prosthesis, to cut a slot in the vertebrae for receiving the fin 18 shown in FIG. 1 and can be used to locate the final disc prosthesis at a desired location with respect to the adjacent vertebrae. The intervertebral disc prosthesis of FIG. 1 is shown as one example of the type of disc shape that can be used for TDR procedures and for which the robotic systems described herein can be used. Other intervertebral discs of other configurations can also be used. Additional optional steps which can be included in the robotic implantation method and can be robotically controlled included marking a midline of the vertebrae, removal of the natural disc and cartilage and shaping the bone.

Figure 2:
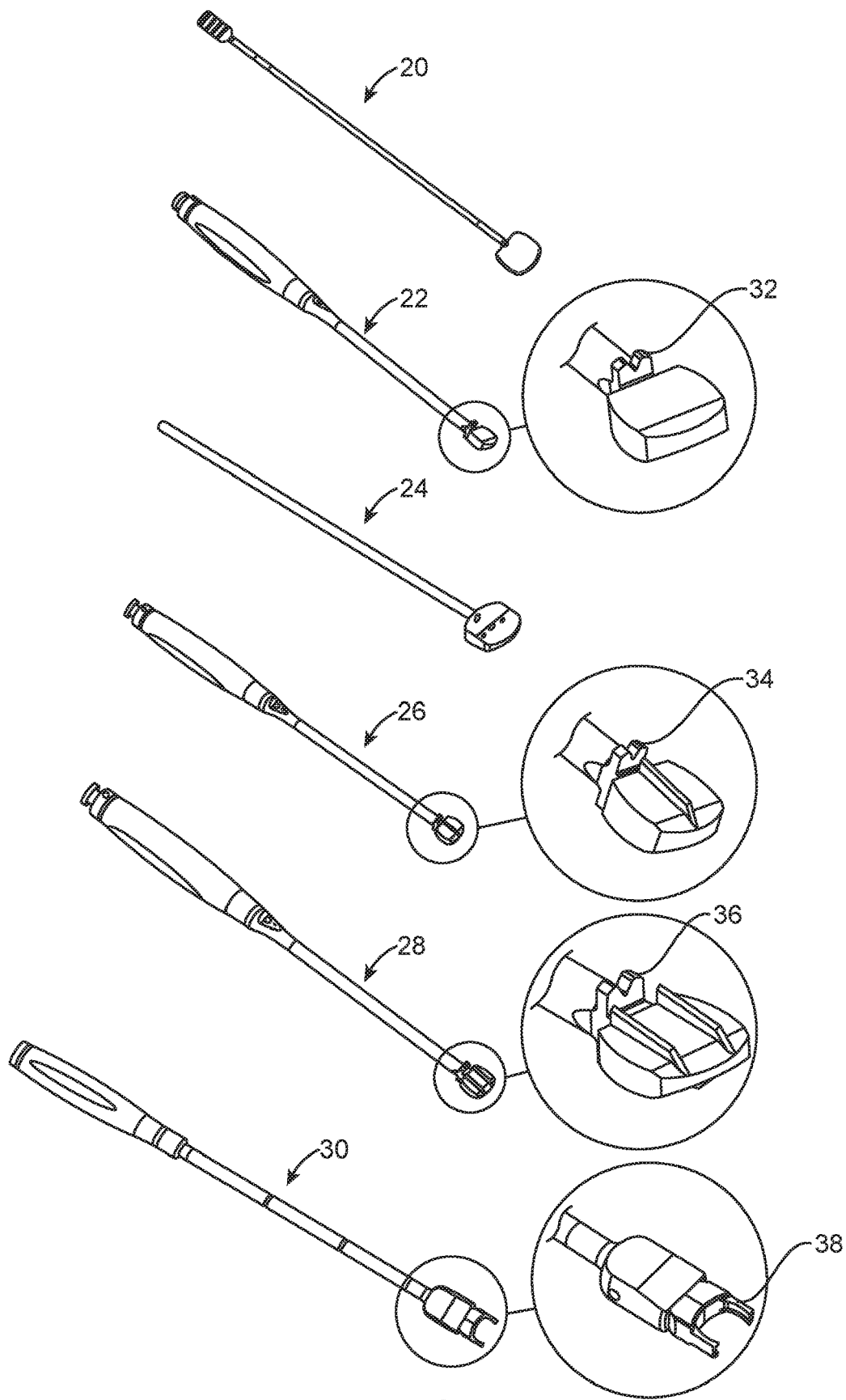
FIG. 2 is a perspective view of set of intervertebral disc prosthesis implantation instruments.

FIG. 2 is a perspective view of set of intervertebral disc prosthesis implantation instruments for use in selecting a disc prosthesis size, cutting a slot for the disc prosthesis and implanting the disc prosthesis into the patient. The instruments illustrated in FIG. 2 include a footprint sizer 20, a height sizer or distraction wedge 22, a midline finder 24, a single slot cutter 26, a dual slot cutter 28 and a placement instrument 30. The instrument set shown in FIG. 2 can be used for either a manual implantation procedure, a partially robotic implantation procedure or a fully robotic implantation procedure. Each of the instruments illustrated are examples of instruments that would be included in the set. The actual instrument set will include multiple sizes of each type of sizer and may include multiple cutters and placement instruments.

The instrument set is provided with two or more footprint sizers 20 which are in the form of flat plates in the shape of the disc prosthesis endplates and correspond in size to the range of vertebral endplate sizes. Each sizer is attached to the distal end of a long thin rod handle. Once a thorough discectomy and endplate preparation has been performed, the footprint sizers are inserted into the disc space starting from the smallest size and progressing to the larger sizes until the size that most closely matches the bony endplate geometry is determined. The footprint sizing step can also precede the endplate preparation step.

The height sizers 22, sometimes called distraction wedges, also come in heights which correspond to the range of implant heights which are available. The height sizers can be provided in one size or in each of the different footprint sizes. The height sizers are used to separate the vertebral bodies prior to implant insertion and are used progressively, beginning with the smallest height, to determine the optimal height to fit the patient's anatomy. The height sizers 22 have tapered wedge shaped forward edges to aid insertion. Each height sizer is fitted with a safety stop 32 on the proximal end of the instrument sizing head to ensure the sizer is not advanced posteriorly too far into the disc space. The height sizers 22 should be advanced into the vertebral disc space until the desired position is achieved or the safety stop rests anteriorly against the vertebrae. The handle also has a mating feature for attachment of a slaphammer. In a manual method or robotically guided method the height sizers are tapped into place with a slaphammer or a mallet until the desired position is reached. In the fully robotic method, the robot provides the impact force to insert the height sizers.

Although separate footprint sizers and height sizers have been shown, one set of implant sizers can be provided with one sizer corresponding to each height, footprint and lordosis available. For example, where three footprints, three heights and two lordosis are available, there would be 18 sizers each corresponding to a different implant. Although the footprint sizing is generally performed prior to or simultaneously with the height sizing, the footprint sizing step can be performed after distraction and height determination.

The midline finder 24 enables the surgeon to accurately assess the position of the spinal midline using fluoroscopic imaging. The midline finder 24 consists of a radiolucent head on a thin handle. Embedded within the head are radiopaque marker pins that are equidistant from the centerline and handle. Visualization of the midline finder 24 on an AP X-ray allows the surgeon to locate the centerline or midline of the two adjacent vertebral bodies to ensure that the intervertebral disc prosthesis is positioned centrally between the two side edges of the vertebrae. The midline finder 24 is an optional instrument and may be replaced by imaging software which determines and marks the vertebral midline on a 3D model of the vertebrae. The midline finding step is particularly important when cutting slots, channels or other features which are centered in the anatomy and is less important when the implant does not require cutting of centered or symmetrically positioned features.

The slot cutters 26, 28 include tapered wedges with protruding transverse osteotomes. The single slot cutter 26 has a single osteotome on each side while the dual slot cutter 28 has two osteotomes on one side and a single osteotome on the other side. The osteotomes correspond to the position of the fins on the endplates of the disc prosthesis and are specific to the particular intervertebral disc prosthesis variation selected. Other arrangements of osteotomes can be used and are designed solely to interface with a particular disc prosthesis. The slot cutters 26, 28 correspond in height with the corresponding height sizes. Each slot cutter 26, 28 is fitted with a safety stop 34, 36 on the proximal end of the instrument to ensure the cutter is not advanced posteriorly too far into the disc space. After the disc space has been distracted and the center line of the disc space determined with the midline finder and marked, such as by means of cautery, the slot cutter 26, 28 is impacted into the disc space using a mallet or slaphammer until the desired position is achieved or the stop 34, 36 engages the anterior edge of the vertebrae. As with the disc sizers, in a manual method or robotically guided method the cutters are tapped into place with a slaphammer or a mallet, whereas, in the fully robotic method, the robot provides the impact force to insert the height sizers. Once the slot cutter is removed, the disc space is ready to accept the placement of the intervertebral disc prosthesis. Although safety stops 32, 34, 36 are shown on the instruments, the robotic guiding device can also act as a depth stop in which case elimination of the stops is preferred so that the depth of instrument insertion is adjustable by the surgeon and controllable by the robot.

The placement instrument 30 is designed to hold the intervertebral disc prosthesis including the endplates and the core together as a rigid construct for insertion as a single unit to a desired position in the disc space. The placement instrument 30 may come preloaded with the disc prosthesis or the prosthesis may be provided on a clip or in a holder for manual or automated attachment to the placement instrument. The placement instrument 30 has a jaw assembly 38 which engages corresponding slots or grooves of the disc prosthesis endplates. Activation of the instrument handle tightens the jaw assembly 38 to lock the jaws on the implant and allows release of the implant by disengaging the jaws. The placement instrument 30 may come in a single size which fits all discs or may be provided in different sizes for different disc sizes. Like the height sizers and slot cutters, the placement instrument handle can have a mating feature for attachment of a slaphammer. A slaphammer or the robot can be used to provide an impact force to the placement instrument 30 to tap the disc prosthesis into position in the spine.

Each of the instruments shown in FIG. 2 can be provided with handles configured to be attached to or grasped by the robot end effector. Optionally, the instrument handles may include both a manual surgeon grasping handle and a robot grasping feature.

Figure 3:
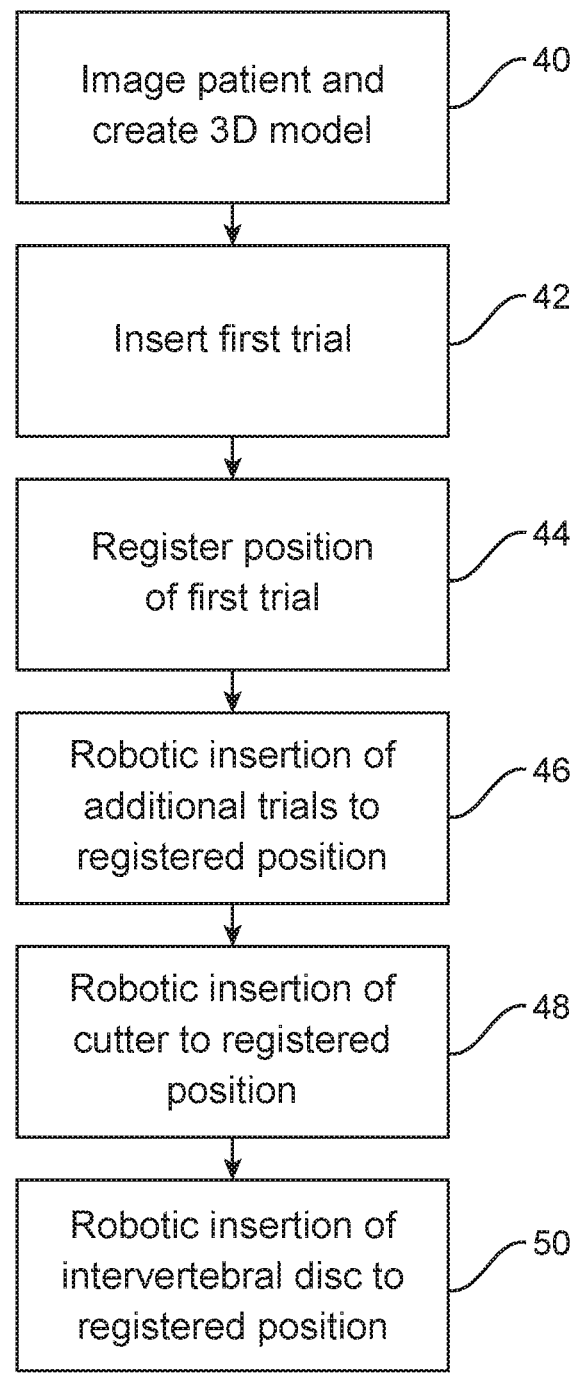
FIG. 3 is a block diagram of a surgical method for robotically selecting and implanting an intervertebral disc prosthesis.

FIG. 3 is a block diagram of a surgical method for robotically selecting and implanting an intervertebral disc prosthesis. As shown in FIG. 3, the surgical method for robotically selecting and implanting an intervertebral disc prosthesis includes a first step 40 of imaging the patient and creating a 3D model. The step of imaging and creating the 3D model will be described in further detail below and may include imaging with X-ray, CT scan, MRI, photographs, infrared camera images or a combination of these methods. Computer software is used to create the 3D model of the first and second vertebrae adjacent the location where the intervertebral disc prosthesis is to be placed and data identifying positions of first and second vertebrae is generated. Position data for the positions of the first and second vertebrae are stored in the computing system for reference in subsequent steps.

Preferably, either before or after the first step of creating the 3D model and prior to the process of selecting the disc prosthesis, the disc space between the two vertebrae is distracted and the natural disc is removed by discectomy.

In one embodiment, the distraction step can be performed robotically. A robotic distraction process is described further in U.S. Provisional Patent Application No. 62/735,710 filed on Sep. 24, 2018 and titled "Robotic Systems and Methods for Distraction for Intervertebral Disc Prosthesis Placement" and in co-pending U.S. patent application Ser. No. 16/578,968 with the same title filed on even date herewith both of which are incorporated herein by reference. The robotic distractor can be pivotable or articulated to control distances between vertebrae in multiple planes and can avoid over distraction injury while reducing forces on the implant cause by under distraction.

Additionally, the disc space is prepared for receiving an implant by removing the natural disc material and shaping the bone. The disc space can be prepared for disc implantation by a robotic or manual system for preparing bone for an intervertebral disc implant. Robotic systems for preparing the bone for an intervertebral disc prosthesis are described further in U.S. Provisional Patent Application No. 62/735,666 filed on Sep. 24, 2018 and titled "Robotic System and Method for Bone Preparation for Intervertebral Disc Prosthesis Implantation" and in co-pending U.S. patent application Ser. No. 16/578,919 with the same title filed on even date herewith both of which are incorporated herein by reference. As described therein, a robotic bone cutting system can significantly improve accuracy of intervertebral disc prosthesis positioning and thereby reduce the pain and discomfort a patient may experience due to improper disc placement. These robotic bone cutting systems can give surgeons confidence in the accuracy of disc positioning, decrease surgery and anesthesia time and reduce blood loss.

In a second step 42, the surgeon or robot inserts a first of a series of trials or sizers starting from the smallest size or if preoperative planning has been performed, with the closest matching trial sizer. The first trial sizer is adjusted either manually by the surgeon or robotically under surgeon control until the sizer is positioned between the adjacent vertebrae at a desired location for implanting the disc prosthesis with respect to the positions of the first and second vertebrae. This desired position for the intervertebral disc prosthesis location is recorded as a registered location in step 44. The desired position is where the disc prosthesis center of rotation is located at the midline of the adjacent vertebral bodies in the lateral direction and slightly posterior of the midline in the anterior posterior direction. Alternately, the natural disc center of rotation can be determined by a motion study of the 3D model and can be used as the desired position or registered position.

In one alternative embodiment, the first trial can be selected by preoperative planning from the 3D model of the patient's spine. One example of a method for imaging the anatomy of the spine and selecting a spinal implant size based on the imaging data is describe in U.S. Pat. No. 7,542,791.

The registered position determined in step 44 is recorded with respect to the positions of the two adjacent vertebrae so that the robot can return a next instrument to the registered position. The registered position can be identified by the location of the center of the posterior edge of the instrument or implant or alternatively by the center of rotation of the implant. Other methods for identifying a registered position can also be used including any one or more surface of the instrument head or any one or more point on the instrument as would be understood by one of ordinary skill in the art.

Whether the first trial implant is inserted by robot or manually, additional trial implants are inserted to the registered position by the robot or manually through a robot guidance arm in step 46. The robotic system moves sequentially from the smallest trial inserted to larger trials until desired fit is achieved. Sometimes it is necessary to reinsert the same trial a second or additional time after the surgeon removes it to further prepare the surgical site such as by removing osteophytes, releasing the posterior ligament, or removing a portion of the uncinate process. The robotic system significantly decreases surgery time by allowing the surgeon to very quickly reinsert the same instrument into the same location within the disc space.

Surgical robots generally operate in one of the following approaches: 1) robot guidance; 2) automated robotic operation; or 3) surgeon guided robotic operation. Examples of the robot guidance approach include the Mazor Renaissance robot and the Globus ExcelsiusGPS robot which both allow instruments to be positioned and screws to be placed through a rigid robotic arm that aligns to the patient according to a surgeon's plan. Another example robotic guided operation is the Stryker Mako robot. The Mako System assists in performing surgery based on a personalized pre-operative plan prepared by the surgeon and then the surgeon guides the robotic-arm within a pre-defined area defined in the preoperative plan. With robot guidance, the robot does not move or activate the instrument, but provides a guide tube which aligns the instrument to the surgical site.

Surgeon controlled robotic surgery systems allow the surgeon's hand movements to be translated to movements within the patient's body. An example of one such surgeon controlled system is the da Vinci System by Intuitive Surgical. The da Vinci System includes a surgical robot and a separate console where the surgeon sits and operates the robot's controls while looking at a magnified image of the surgical site on a monitor.

The sequential insertion of the additional trials in step 46 can be robotically guided or surgeon guided as in the systems described above or can be fully robotic. As each trial is inserted the best fit is determined for a height, footprint size and/or lordosis for the intervertebral disc prosthesis based on the fit in the spine. When desired fit is achieved step 46 is complete. Fit of the trial can be verified by visual, tactile, radiographic and/or other feedback.

As additional trials are inserted to the registered position in step 46, the surgeon can periodically check the position of the trials by X-ray, fluoroscope or other imaging techniques. The registered position can be adjusted or reregistered in the event that the larger size implant alters the desired position. In addition, between insertions of additional trials it may be desirable to remove some bone or shape the vertebrae to better fit the implant shape. This shaping of the bone may change the desired position and the registered position can be updated or adjusted accordingly.

In traditional manual intervertebral disc prosthesis surgery, the tightness of the trial in the disc space and the amount of force required to insert the trial are considered by the surgeon in determining fit. For example, an excessive amount of force to insert the trial would indicate to the surgeon that the trial disc is too tall for the space and a lower height implant would be selected. The fully robotic insertion of the trials can include measurement of the insertion force with the robot. The insertion force is displayed on the surgeon interface for surgeon review. When high insertion force is shown on the surgeon interface, the surgeon can identify the tightness of the trial in the disc space and can choose to select a lower height disc.

Once the disc prosthesis size has been selected, the cutter is robotically inserted in step 48 to the registered position identified in step 44 or the adjusted registered position identified in step 46. The cutter controlled or guided by the robot is impacted by a mallet or by robotic impact to create a slot or multiple slots. The depth of the slot is controlled by the robot by inserting the cutter only to the registered position and not beyond. The insertion of the cutter in step 48 can be robotically guided or surgeon guided as in the systems described above or can be fully robotic. The cutting step 48 is an optional step and needed only where the selected disc prosthesis shape is a disc with a fin or other projection which is received in the slot(s) cut in the vertebrae. Although the cutter has been shown to cut a slot or channel, other shaped cutters can also be used for making other cuts as needed for a particular implant.

After the slot has been cut if necessary in step 48, the intervertebral disc prosthesis is inserted into the space between the vertebrae to the registered position in step 50. The insertion of the disc prosthesis with the placement instrument in step 50 can be robotically guided or surgeon guided as in the systems described above or can be fully robotic. In a fully robotic system, the robot can place the disc prosthesis at the registered position and then disengage the placement instrument from the disc prosthesis and remove the placement instrument. In one alternative system, the robot system can control the trajectory of the placement instrument while the surgeon controls sequential advancement. For example, the surgeon can indicate the distance to insert in a sequential manner such as by moving 2 mm at a time for initial insertion and then adjusting 1 mm or 0.5 mm at a time when approaching a final position. Insertion force feedback from the robot can also be used by the surgeon in determining when the final position has been reached. When insertion force above a threshold is determined, the computer system can display a high force warning to the surgeon. In turn, the surgeon can determine whether the high force indicates that the disc should not be inserted further into the disc space due to the risk of having low mobility.

Figure 4:
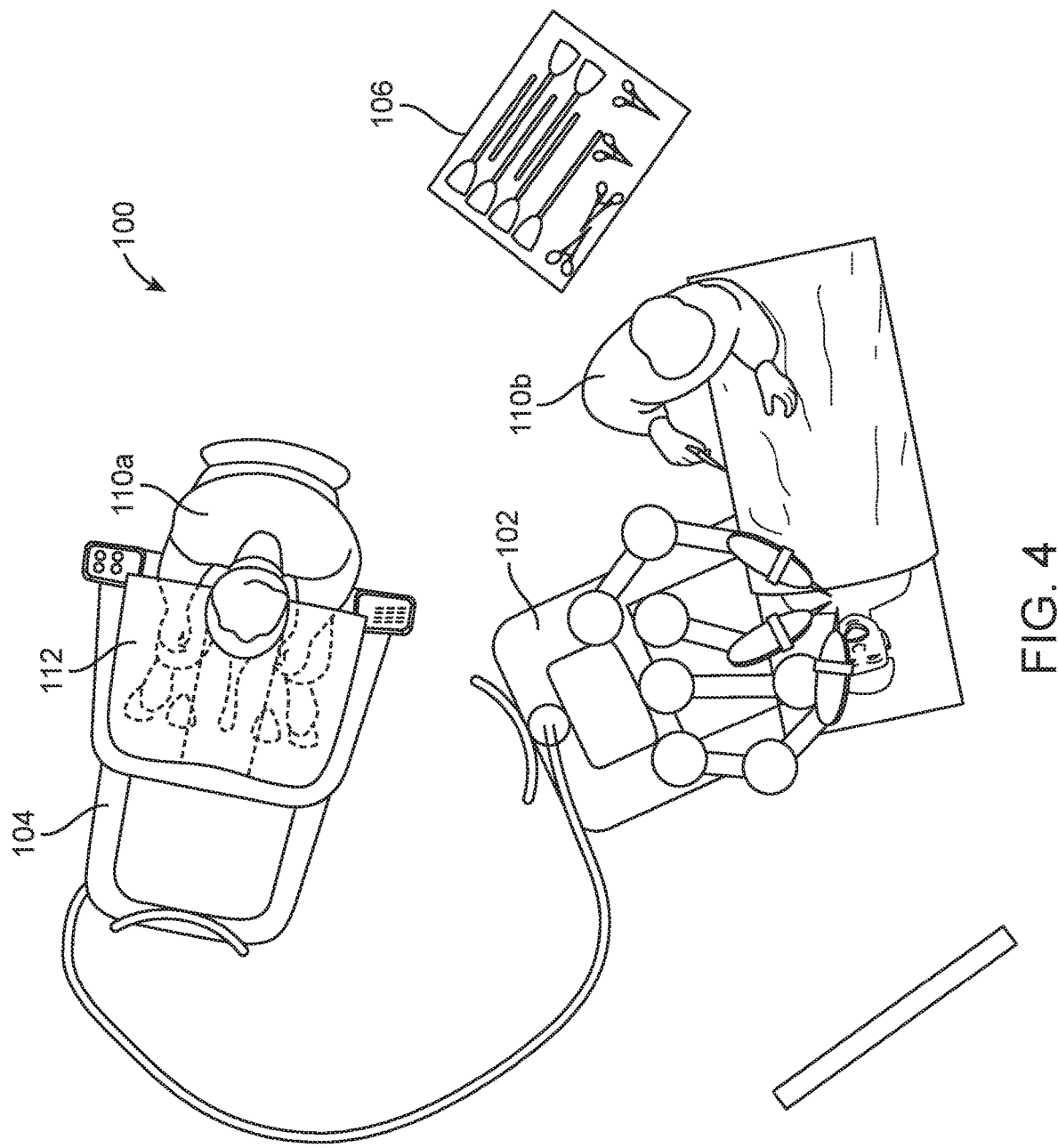
FIG. 4 is a schematic view of a surgical system for robotically selecting and implanting an intervertebral disc prosthesis.

FIG. 4 is a schematic view of a surgical system 100 for robot assisted intervertebral disc selection and implantation. The surgical system 100 includes a robot 102 for positioning instruments or guiding instruments, an imaging device (not shown), such as a fluoroscope on a C-arm, and a computer system 104 or processing system. Preoperative or intraoperative images taken with the imaging device or other imaging system allow the computer system 106 to generate and store position data for the positions of the first and second vertebrae.

The surgical system 100 identifies positions of the first and second vertebrae with the imaging system and generates and stores position data for the positions of the first and second vertebrae in a 3D model in the computer system 104. An instrument tray 106 is provided with surgical instruments, such as those shown in FIG. 2, needed for the disc prosthesis implantation procedure including sizing, cutting and placement instruments. The robot 102 inserts a first trial instrument between the first and second vertebrae to get an initial registration position with respect to the first and second bones and storing position data. The first trial can be grasped by the robot from the instrument tray 106 robotically or can be attached to the robot end effector by the surgeon or surgeon's assistant. The initial registration position is first determined with a first trial placed either manual by the surgeon, automatically by the robot, or manually with robot guidance. The registration position stored in the computer system 104 is a desired location for implantation of the selected intervertebral disc prosthesis with respect to the positions of the first and second vertebrae. The robot 104 then sequentially delivers a plurality of instruments including sizing templates, additional trials, cutters or placement instruments with the robot 104 to the initial registration position. In the case of FIG. 4, the initial registration position is the disc space between two vertebrae in the cervical spine accessed from the anterior side of the spine. However, the robotic surgical system 100 can also be used for the lumbar and thoracic spine and for access from the posterior or lateral aspects of the spine.

FIG. 4 illustrates two potential locations for a surgeon and a surgeon's assistant with respect to the surgical system 100. In one alternative system, the surgeon 110*a* controls the robotic surgery system from a control center 112 of the computer 104. The control center 112 allows the surgeon's hand movements to be translated to movements within the patient's body. With this system, the surgeon's assistant can provide assistance with attaching the appropriate instruments to the robot.

In another robot system, the control center 112 is eliminated and a surgeon 110*b* operates the robot by attaching the appropriate instruments into the robot and controlling the instruments and robot at the side of the patient. The surgeon can be provided with foot petal or hand controls for activating the robot and instruments in the case of a placement instrument that requires activation to release the disc from the placement instrument. The surgeon can also be provided with one or more monitors for the computer system 104 which are visible from the surgeon position at the side of the patient.

Figure 5:
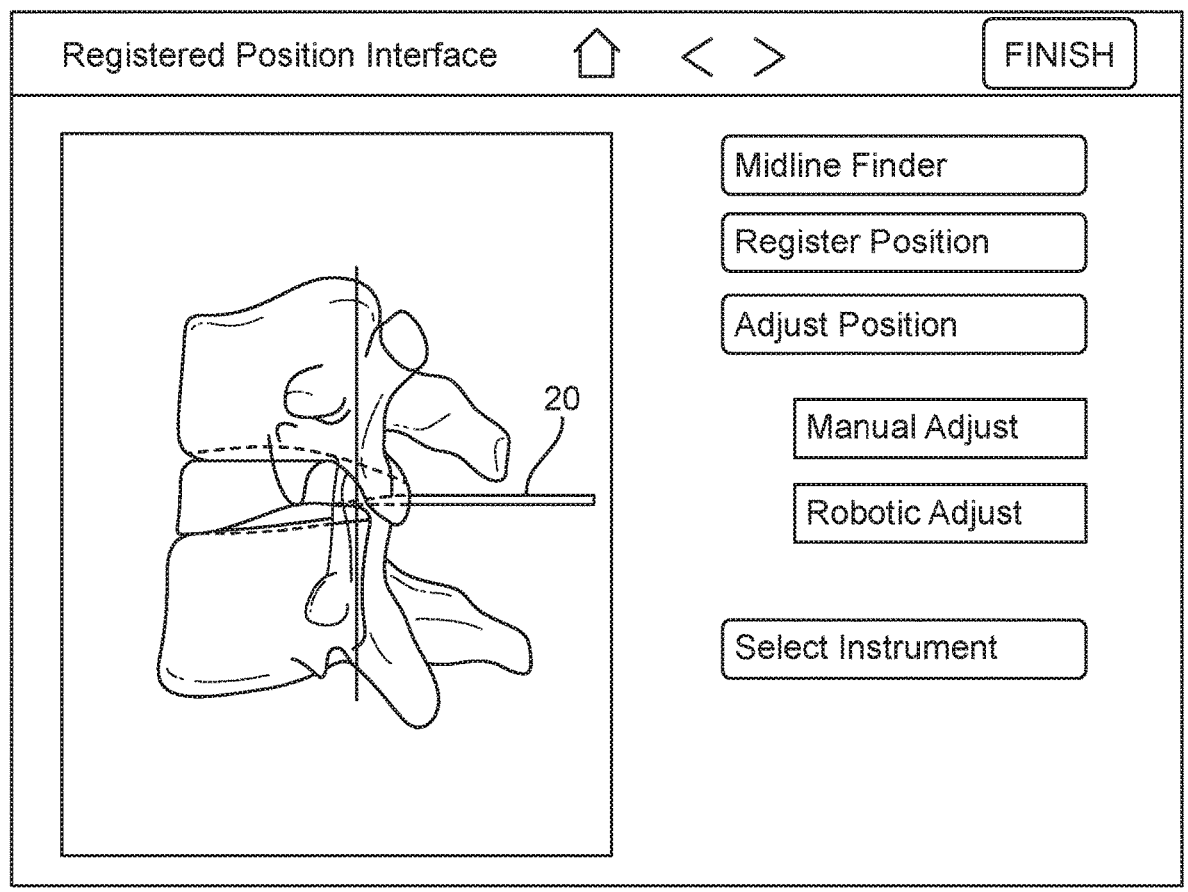
FIG. 5 is a view of a display interface showing a 3D model of two adjacent vertebrae and an instrument at a registration position.

FIG. 5 is a view of a display interface showing a 3D model or an X-ray image of two adjacent vertebrae during surgery. An instrument 20, such as a sizing instrument, is shown inserted between the vertebrae to determine the registered position for insertion of additional instruments. The display interface of FIG. 5 is one example of a computer interface which can be displayed on a computer monitor, laptop computer, tablet or other device (e.g. heads-up display, augmented reality display) and used in selecting an intervertebral disc prosthesis and placement of the selected intervertebral disc prosthesis. The interface of FIG. 5 includes options for finding a midline, registering a trial position, adjustment of the trial position and selection of an instrument. Other options which may be available include determination of center of rotation location. The three dimensional image of the vertebrae on the left side of the interface can be rotated by the user to view different angles.

Although FIG. 5 shows a single three dimensional image of the vertebrae which is rotatable, the computer interface alternatively can include 2, 3, or 4 orthogonal views as well as one or more trajectory views of the vertebrae. Other computer interfaces can include separate interfaces for the steps of position registration, selection of instrument and position adjustment.

Imaging Systems

The methods of creation of the 3D model of the vertebrae and location of and tracking of the vertebrae described herein are examples of the systems that may be used. The surgical methods are not meant to be limited to any particular imaging methods or systems and bone tracking methods. The imaging system generates a 3D model of at least the vertebrae above and below the natural disc to be replaced and can also generate a 3D model of additional anatomic structures. This 3D model can be based on a number of different imaging modalities including imaging with X-ray, CT scan, MRI, photograph or a combination of these methods. The images can be taken preoperatively, intraoperatively or a combination thereof.

In one example, a preliminary 3D model of the anatomical area for surgery is created from preoperative CT scan data. Software or the surgeon can use the preliminary 3D model to make a preliminary determination of the intervertebral disc prosthesis to be selected. This preoperative planning can be used to reduce actual surgery time by having an increased chance of selecting the correct disc in a first try. Once the patient is in surgery, markers are attached to the vertebrae above and below the natural disc to be replaced to allow precise identification of the position and orientation of both of the vertebrae throughout surgery. The 3D model is updated with intraoperative fluoroscopic image data or other image data of the vertebrae having the markers to allow real time 3D tracking of the precise position of the vertebrae throughout surgery.

The radiopaque markers, reflective fiducials, mapped bone surfaces or registration of anatomical features allows the imaging system to identify positions of first and second vertebrae and generate and store position data for the positions of the first and second vertebrae in a computing system which transmits this information to a robot control system. The positions of the first and second vertebrae determined from the 3D model of first and second vertebrae at a location of a disc to be replaced from pre-operative and/or intraoperative imaging techniques are used in the subsequent steps of robotic controlled disc selection and implantation. Preferably, the imaging system will continuously update and verify the positions of the first and second vertebrae throughout the step of robotically guiding the instruments into to the surgical site to adjust for any change in position of the vertebrae. As the bones can move independently of one another, the positions of bones should be verified. Particularly when the trial or other instrument fit is a tight fit requiring significant force from the robot or surgeon to insert the trial or other instrument the bones may shift during the process. Adjustment of the registered position to account for this shift of the bones is provided by the computer system.

The radiopaque markers, reflective fiducials, mapped bone surfaces or registration of anatomical features allows the imaging system to identify positions of first and second vertebrae and generate and store position data for the positions of the first and second vertebrae in a computing system which transmits this information to a robot control system. The positions of the first and second vertebrae determined from the 3D model of first and second vertebrae at a location of a disc to be replaced from pre-operative and/or intraoperative imaging techniques are used in the subsequent steps of robotic controlled disc selection and implantation. Preferably, the imaging system will continuously update and verify the positions of the first and second vertebrae throughout the step of robotically guiding the instruments into to the surgical site to adjust for any change in position of the vertebrae. As the bones can move independently of one another, the positions of bone bones should be verified. Particularly when the trial or other instrument fit is a tight fit requiring significant force from the robot or surgeon to insert the trial or other instrument the bones may shift during the process. Adjustment of the registered position to account for this shift of the bones is provided by the computer system.

The imaging system used can be any of the existing image guided surgery systems.

Determination of Trial Fit by Robot Insertion Force Feedback

Typically in disc prosthesis surgery, fit of the trials can be verified by visual, tactile, radiographic and/or other feedback. The tightness of the trial in the disc space and the amount of force required to insert the trial are considered by the surgeon in determining fit. In one version, the robot of the surgical robot system is provided with force transducers which can measure the insertion force with the robot as the trials are inserted. This insertion force can be displayed on the surgeon interface. When insertion force above a threshold is determined, the computer system can display a high force warning. In turn, the surgeon can select a lower height disc to reduce the tightness, distract the disc space further to reduce the tightness, or take other action as deemed necessary by the surgeon.

Registration of Position by Posterior Edge of Trials and Implant

The depth of insertion of an intervertebral disc prosthesis is important to successful performance of the implant and pain relief for the patient. The correct position for the posterior edge of the implant is where the posterior edge does not extend beyond the posterior margin of either of the vertebrae while the center of rotation is slightly posterior of the center point of the vertebrae. Therefore, some surgeons may choose to register the position of each of the trial instruments, the cutter and the eventual implant by registration of the posterior edge of the instrument or implant with respect to the vertebrae. Registration of positon with respect to the posterior edge of the instruments and implant will prevent the implant from extending too far posterior while getting the implant as far posterior within the disc space as possible to avoid potential expulsion due to positioning too far anterior.

The degree of precision required in returning the robot to the registration position in subsequent steps varies depending on the surgical procedure. For cervical disc replacement, a registration accuracy within <0.5 mm is needed (accuracy of <0.3 mm preferred), while for lumbar disc replacement a precision of <1.0 mm may be sufficient (accuracy of <0.6 mm preferred). The robotic system generally incorporates a computer guided navigation system which has it's own accuracy in addition to the accuracy of the robot itself.

Registration of Position by Center of Rotation of Trials and Implant

In an alternative process, the registration of the position of the trial instruments, cutters and implant is by the center of rotation. Positioning of the intervertebral disc prosthesis center of rotation at a natural center of rotation for the segment of the spine can be important. Certain intervertebral disc prostheses of the ball and socket type are particularly sensitive to requiring placement with the disc center of rotation at or very close to the spinal segment center of rotation. Since the anatomical center of rotation cannot be determined based on visible landmarks, automated systems for determining natural anatomical center of rotation and locating the intervertebral disc prosthesis center of rotation at the natural anatomical center of rotation would be useful. Placement of the intervertebral disc prosthesis center of rotation in a non-natural anatomical position can create improper motion and lead to other unintended problems for the patient such as increased forces on adjacent tissues and adjacent vertebral discs.

Registration of positon of the trials and instruments with respect to the center of rotation of the implant will most closely match the center of rotation of the implanted disc prosthesis to the natural center of rotation of the segment of the spine. In order to register each instrument with respect to the center of rotation, the instruments, including the trials and cutters, each have a known location corresponding to the center of rotation of the implant. The center of rotation location can be marked on the instruments, for example by a radiopaque marker, or can be saved in the computer system relative to the instrument attachment to the robot.

Selecting Between Robot Controlled Motion and Surgeon Controlled Robot Guided Motion The robotic system provides for both robot controlled motion and robot guided motion of the instruments. In one system, a user can select between automatic (robotic) motion and robotic guided manual motion of the instruments with respect to the bones. In some cases, the system provides only one of these options for various reasons, such as, only one option is applicable to the situation or only one option is approved for use in the circumstances. If the robotic control of the instruments is chosen, the robot end effector grasps the appropriate cutting device and manipulates the surgical instrument to robotically enter the surgical site. In a method of robotic control of the surgical instrument the robot is controlled to move the instrument into and out of the surgical site without a surgeon's hand on the instrument. Surgeon oversight of the robotic procedure can be provided with the surgeon positioned beside the patient having an off switch or pedal adjacent the surgery.

If the robotic control of a guiding device is selected, a guiding device is connected to the robot end effector and positioned by the robot with respect to the patient. The surgical instruments are then positioned in or grasped by the guiding device. In this method, the surgeon controls the instruments while supported by the guiding device such that the location of the instrument is robotically controlled by the guiding device. In one option, the robotic guiding device acts as both a depth stop to control the depth of insertion or cutting and a trajectory control to allow insertion only in a desired trajectory.

Robot End Effectors

End effector is a generic term that includes all the devices that can be installed at a robot wrist. End effectors which can be used in the present application include grippers, such as pneumatic, hydraulic and servo-electric grippers. End effectors with tool changers can also be used when many different tools need to be used in sequence by one robot. They are used to standardized the interface between the robot flange and the base of the tool. Tool changers can be manual or automatic. Force-torque sensors can be installed between the robot flange and the surgical instrument that interacts with the patient's anatomy. Torque sensors measure the force and torque that the robot applies to the anatomy through the tool. 6 axis force-torque (FT) sensors can be used to measure 3 force components (x-y-z) and 3 torques around those axes. FT sensors are particularly useful for controlling insertion to not exceed a maximum force or a maximum torque in one or more direction.

Although the robotic surgical systems and methods have been described for use in selection and implantation of an intervertebral disc prosthesis, the systems and methods described herein may also be used for improved precision and optimal performance of other spinal implants including interbody fusion devices, interspinous spacers, vertebral body replacements. The robotic surgical systems and methods can be used to assist the surgeon in increasing speed and precision in implanting these other implants. Robot assisted implant selection and implantation can be particularly advantageous in multi-level surgical procedures where the intricacy of the procedure increases.

Modification of the above-described assemblies and methods for carrying out the invention, combinations between different variations as practicable, and variations of aspects of the invention that are obvious to those of skill in the art are intended to be within the scope of the invention disclosure.

What is claimed is:

1. A surgical method for robot assisted intervertebral disc prosthesis placement, the method comprising:
   identifying positions of first and second vertebrae and generating and storing position data for the positions of the first and second vertebrae in a 3D model in a computing system;
   inserting a first trial instrument between the first and second vertebrae to obtain an initial registration position with respect to the first and second vertebrae, wherein the initial registration position is a desired location for an intervertebral disc prosthesis with respect to the positions of the first and second vertebrae; and
   sequentially delivering a plurality of instruments including sizing templates, trials, cutters or placement instruments with a robot to the initial registration position, wherein the computing system includes an interface including a user-selectable option for selecting one of-the plurality of instruments to be sequentially delivered with the robot to the initial registration position.

2. The surgical method of claim 1, wherein the initial registration position is adjusted during the sequential delivery of the plurality of instruments to provide an adjusted registration position, wherein the adjusted registration position is used for delivery of subsequent instruments.

3. The surgical method of claim 1, further comprising monitoring the sequential delivery of the plurality of instruments by a robotic force sensing system, wherein the robotic force sensing system is configured to detect a force needed to insert the plurality of instruments to the initial registration position.

4. The surgical method of claim 3, further comprising pausing the sequential delivery when the force sensing system detects a force exceeding a force limit.

5. The surgical method of claim 1, wherein the robot delivers the plurality of instruments to the initial registration position with an accuracy within less than 0.5 mm.

6. A system for robot assisted intervertebral disc prosthesis placement, the system comprising:
  a 3D modeling system for creating a 3D model of first and second vertebrae adjacent a disc space and identifying positions of the first and second vertebrae and generating and storing position data for the positions of the first and second vertebrae;
  a computing system for storing and processing the 3D model and the position data;
  a robot;
  a plurality of instruments including sizing templates, trials, cutters or placement instruments for intervertebral disc prostheses, wherein each of the plurality of instruments is configured to be coupled to the robot, wherein the plurality of instruments includes a first trial instrument configured to be inserted between the first and second vertebrae to obtain an initial registration position, wherein the initial registration position is a desired location for an intervertebral disc prosthesis with respect to the positions of the first and second vertebrae; and
  an interface on the computing system, the interface including a user-selectable option for selecting one of the plurality of instruments to be sequentially delivered with the robot to the initial registration position.

7. The system of claim 6, wherein the robot includes a guiding device which guides a trajectory of the plurality of instruments and provides a depth stop to limit a depth of insertion of the plurality of instruments.

8. A surgical method for robot assisted intervertebral disc prosthesis placement, the method comprising:
  identifying positions of first and second vertebrae and generating and storing position data for the positions of the first and second vertebrae in a 3D model in a computing system;
  identifying a desired location of an intervertebral disc prosthesis either by preoperative or intraoperative planning; and
  inserting the intervertebral disc prosthesis between the first and second vertebrae to the desired location between the first and second vertebrae with robotic guidance,
  wherein the computing system includes an interface including a user-selectable option for selecting an instrument to be sequentially delivered with the robot to the desired location of the intervertebral disc prosthesis.

9. The surgical method of claim 8, further comprising creating the 3D model in the computing system using 3D imaging of a patient being subjected to the robot assisted intervertebral disc prosthesis placement.

10. The surgical method of claim 1, wherein the interface further includes an option for finding a midline of the first and second vertebrae.

11. The surgical method of claim 1, wherein the interface further includes an option for determining a center of rotation of the intervertebral disc prosthesis.

12. The surgical method of claim 11, further comprising registering a position of the first trial instrument with respect to the center of rotation of the intervertebral disc prosthesis.

* * * * *